United States Patent [19]

Behrmann et al.

[11] 4,071,576
[45] Jan. 31, 1978

[54] PROCESS FOR REGENERATING FLUOROSULFURIC ACID CATALYST

[75] Inventors: William C. Behrmann; Robert H. Caulk, both of Baton Rouge, La.

[73] Assignee: Exxon Research & Engineering Co., Linden, N.J.

[21] Appl. No.: 772,643

[22] Filed: Feb. 28, 1977

[51] Int. Cl.² .............................................. C07C 3/54
[52] U.S. Cl. .......................... 260/683.47; 260/683.58; 252/415
[58] Field of Search .................. 260/683.47, 683.58, 260/683.48, 683.62; 252/415, 411 R

[56] References Cited

U.S. PATENT DOCUMENTS

| | | | |
|---|---|---|---|
| 3,766,293 | 10/1973 | Parker et al. | 260/683.58 |
| 3,925,318 | 12/1975 | Parker et al. | 260/683.58 |
| 4,033,899 | 7/1977 | Bennett et al. | 252/411 R |

Primary Examiner—George Crasanakis
Attorney, Agent, or Firm—John W. Ditsler

[57] ABSTRACT

The deactivated fluorosulfuric acid catalyst in olefin-paraffin alkylation is regenerated by (1) contacting the acid phase with water to form an acid-water mixture (2) stripping the acid-water mixture with a paraffin to form a gaseous phase of hydrogen fluoride and paraffin (3) cooling the gaseous phase with liquid paraffin to form a liquid fluorosulfuric acid and a vapor containing fluorosulfuric acid, hydrogen fluoride and paraffin (4) treating the vapor with liquid SO₃, and utilizing liquid fluorosulfuric acid in the treating step in countercurrent flow to the vapor to convert the hydrogen fluoride to regenerated fluorosulfuric acid, (5) the remaining gas phase containing paraffin and a minor amount of fluorosulfuric acid is cooled to condense all the fluorosulfuric acid to liquid and (6) the regenerated liquid fluorosulfuric acid is used as the countercurrent flowing liquid fluorosulfuric acid in treating step (4).

18 Claims, 1 Drawing Figure

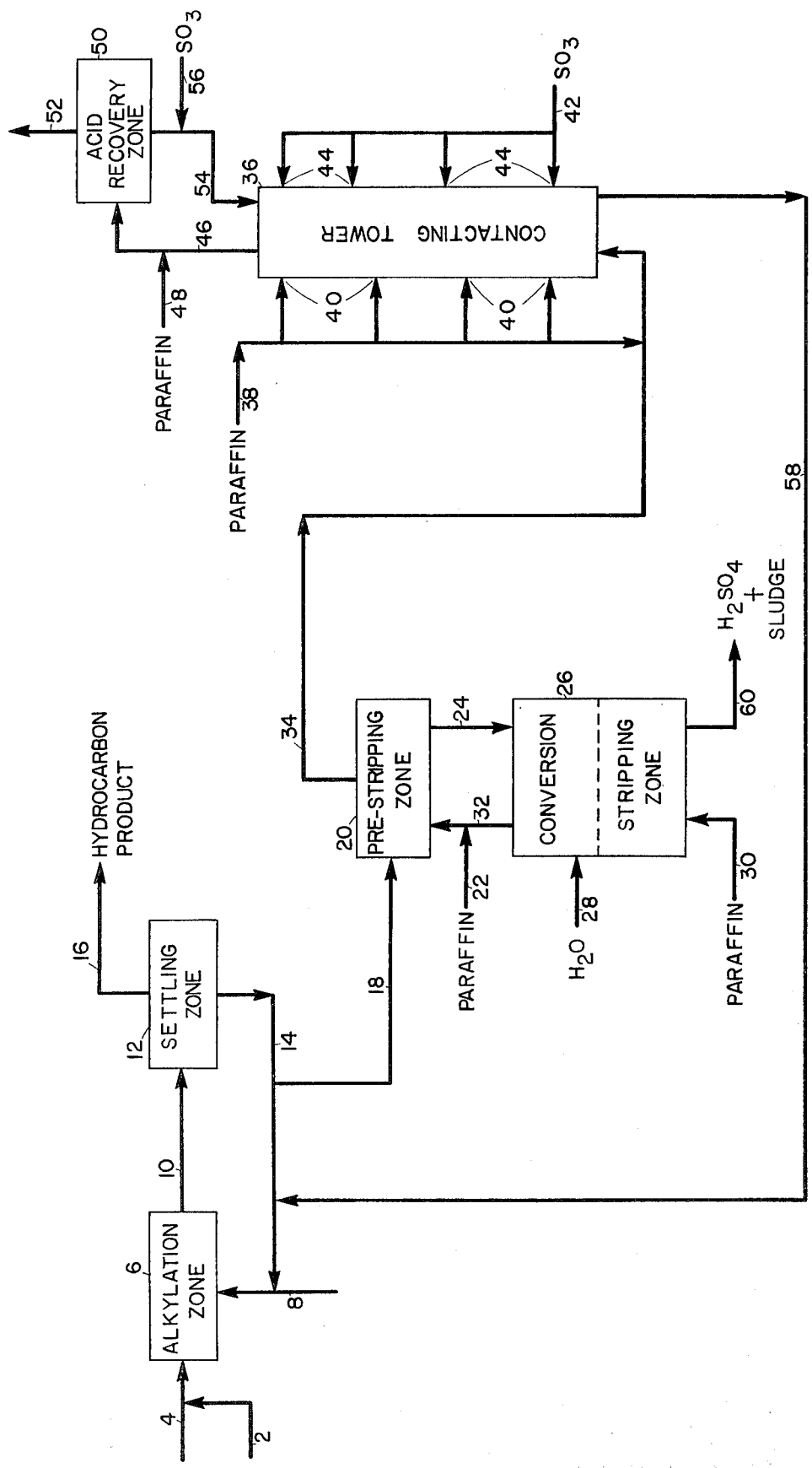

PROCESS FOR REGENERATING FLUOROSULFURIC ACID CATALYST

BACKGROUND OF THE INVENTION

1. Field of the Invention

The present invention relates to a process for regenerating a catalyst of the type used in hydrocarbon conversion processes. More particularly, this invention relates to a process for regenerating a catalyst comprising fluorosulfuric acid, said catalyst having become at least partially deactivated due to the formation of dilvents during contact with a hydrocarbon feedstock in an alkylation process.

2. Description of the Prior Art

It is well known in the prior art that as the alkylation reaction proceeds, an organic material will form and will accumulate in the fluorosulfuric acid catalyst phase. The material has been given a variety of names including red oil, sludge, organic sludge, acid-oil and the like. This organic material is a natural by-product of acid-catalyzed hydrocarbon reactions such as occur during alkylation and has been described in the literature as a conjunct polymer (see Miron, S. and Lee, R.J., "Molecular Structure of Conjugated Polymers", J. Chem. Eng. Data, Vol. 8, pp. 150-160 1963), the disclosures of which are incorporated herein by reference. These conjunct polymers are complex mixtures of olefinic, conjugated cyclic hydrocarbons that may be formed from any type of hydrocarbon except aromatics. More specifically, they are believed to be cyclic polyolefinic hydrocarbons with a high proportion of conjugated double bonds, no two of which are in the same ring. Five membered ring systems predominate, but larger, and possibly also smaller, rings are believed to be present. The accumulation of this material will ultimately cause the activity of fluorosulfuric acid catalysts to decline until said catalysts cease to exhibit economic activity. In such cases, depending upon economic factors, the catalyst may be replaced or regenerated to restore desired activity levels.

One method for regenerating catalysts comprising fluorosulfuric acid has been suggested in U.S. Pat. No. 3,766,293, the disclosures of which are incorporated herein by reference. According to this method, an alkylation catalyst comprising fluorosulfuric acid, at least a portion of which has become deactivated, may be regenerated by (1) contacting said catalyst with water so as to convert at least a portion of the fluorosulfuric acid to hydrogen fluoride and sulfuric acid; (2) removing at least a portion of the hydrogen fluoride from said catalyst by contacting the same with a paraffin so as to form a hydrocarbon phase containing hydrogen fluoride; and (3) treating said hydrocarbon phase with sulfur trioxide to regenerate the fluorosulfuric acid. In application Ser. No. 772,637 filed on the same date herewith, there is disclosed a method for regenerating fluorosulfuric acid catalysts which employs refrigeration and cooling of the hydrocarbon phase to provide a stripping gas of low fluoride content. While the above methods are effective in regenerating said catalyst, it is believed that the particular regeneration technique described hereinbelow has certain advantages over those disclosed in U.S. Pat. No. 3,766,293 and application Ser. No. 772,637, which heretofore have not been disclosed.

SUMMARY OF THE INVENTION

Now according to the present invention, a process has been discovered for regenerating a deactivated or partially deactivated alkylation catalyst comprising fluorosulfuric acid, said deactivated or partially deactivated catalyst containing an organic sludge formed during said alkylation process, which comprises:

1. contacting said deactivated or partially deactivated fluorosulfuric acid with water to form an acid-water mixture, thereby converting at least a portion of the fluorosulfuric acid contained therein to hydrogen fluoride and sulfuric acid;

2. removing at least a portion of the hydrogen fluoride from said acid-water mixture formed in step (1) by contacting same with a paraffin to form a gaseous phase containing hydrogen fluoride and paraffin and a liquid phase containing sulfuric acid and sludge;

3. cooling the gaseous phase formed in (2) by contact, in a contacting zone, with liquid paraffin to form a liquid phase containing fluorosulfuric acid and a vapor phase containing fluorosulfuric acid, hydrogen fluoride and paraffin;

4. contacting the liquid and vapor phases formed in (3) with sulfur trioxide dissolved in a liquid stream of fluorosulfuric acid flowing countercurrent to the flow of said vapor phase such that hydrogen fluoride undergoes a substantially liquid phase reaction with said sulfur trioxide to form a liquid phase of regenerated fluorosulfuric acid and a gas phase containing predominantly paraffin with minor amounts of fluorosulfuric acid;

5. cooling further the gas formed in (4) to condense substantially all of the fluorosulfuric acid present therein, thereby forming a liquid phase containing predominantly fluorosulfuric acid and a gas phase containing substantially pure paraffin; and 6. using at least a portion of the liquid phase formed in (5) as the countercurrent flowing fluorosulfuric acid stream in (4). In a preferred embodiment, normal butane is the paraffin and at least a portion of the regenerated fluorosulfuric acid is recycled to the alkylation process. In addition, it is preferred that the paraffin coolant and the sulfur trioxide be introduced into the contacting zone at more than one point along the length of said zone.

The present invention has the advantages of the integrated process claimed in application Ser. No. 772,637 (that of providing a closed system with respect to the stripping gas such that it can be employed independent of the alkylation process during normal operations, including startup and shutdown periods) as well as providing an improved method for combining the stripped HF with makeup $SO_3$ to reconstitute regenerated fluorosulfuric acid. This is effected in a countercurrent contactor which provides for more efficient reconstitution of the fluorosulfuric acid by minimizing the volume of liquid holdup between the liquid acid phase and the hydrocarbon stripping gas, thereby minimizing degradation reactions which facilitate the formation of an organic sludge diluent in the regenerated acid, as is disclosed in application Ser. No. 772,636, filed on the same date herewith. Improved utilization of $SO_3$ during reconstitution is also obtained according to the present invention as well as better utilization of the cooling provided in the process.

BRIEF DESCRIPTION OF THE DRAWING

The single FIGURE is a flow diagram illustrating a preferred embodiment of the present invention.

DETAILED DESCRIPTION OF THE INVENTION

Having thus described the invention in general terms, reference is now made to the FIGURE which shows an alkylation process using a catalyst system such as that described in U.S. Pat. No. 3,887,635, the disclosures of which are incorporated herein by reference. Such details are included as are necessary for a clear understanding of how the present invention may be applied in the regeneration of an alkylation catalyst comprising fluorosulfuric acid, said catalyst being at least partially deactivated. No intention is made to unduly limit the scope of the present invention to the particular configuration shown as variations obvious to those having ordinary skill in the art of alkylation and other unit processes and operations are included within the broad scope of the present invention.

Referring now to the FIGURE, there is shown an olefin stream in line 2 which is, preferably, admixed with a paraffin stream in line 4 before introducing the combined stream into alkylation zone 6. If desired, however, the olefin and paraffin streams can be fed directly into alkylation zone 6. The olefin construction in the feed ranges from 0.5 to 25 volume percent based on total feed and preferably below 10 volume percent. Translated into volume ratios, high volume ratios of paraffin to olefin ranging from 10:1 to 200:1 or higher are preferred, although somewhat lower ratios may be used, e.g. 3:1. Correspondingly high volume ratios of paraffin to olefin are also desired within the alkylation zone. Preferably, the paraffin/olefin ratio therein ranges from about 5:1 to 2,000:1 or higher.

Suitable olefinic reactants include $C_2$-$C_{12}$ terminal and internal monoolefins such as ethylene, propylene, isobutylene, butene-1, butene-2, the pentenes (e.g. trimethylethylene) and similar higher monoolefinic hydrocarbons of either a straight chain or a branched chain structure. Preferably, the $C_2$-$C_6$ monoolefins are used, although the highly-branched $C_7$-$C_{12}$ monoolefins may also be used. The reaction mixtures may also contain small amounts of diolefins and other hydrocarbons normally present in refinery hydrocarbon streams. Although it is desirable from an economic standpoint to use the normally gaseous olefins as reactants, normally liquid olefins may be used. Thus, reactable polymers, copolymers, interpolymers, crosspolymers, and the like, of the above-mentioned olefins, such as, for example, the diisobutylene and triisobutylene polymers, the codimer of normal butylene and isobutylene, may be employed as an olefinic reactant. Mixtures of two or more of the olefins described above can be used as the process feedstock.

$C_2$, $C_3$, $C_4$ and/or $C_5$ olefin cuts from thermal and/or catalytic cracking units; field butanes which have been subjected to prior isomerization and/or partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present alkylation process. Such feeds are preferably dried to control excess water buildup, i.e. to about 5 to 15 wppm or less of water before entering the alkylation zone.

The paraffinic feedstocks that can be reacted with the olefins desirably comprise straight and/or branched chain $C_4$-$C_{10}$ paraffins such as hexane, butane and the like, and preferably $C_4$-$C_6$ isoparaffins such as isobutane, isopentane, isohexane and the like. While open chain hydrocarbons are preferred, cycloparaffins such as methylcyclopentane may also be used.

Returning to the FIGURE, a catalyst comprising fluorosulfuric acid and one or more moderators is shown being introduced into alkylation zone 6 via line 8. Generally, the moderator contains at least one oxygen atom per molecule and includes water, aliphatic and cycloaliphatic alcohols and ethers, aliphatic, cycloaliphatic and aromatic sulfonic and carboxylic acids and their derivatives, inorganic acids and other oxygen containing organic compounds. By the term "moderator" is meant a compound which, in combination with fluorosulfuric acid, produces a catalyst system of reduced acidity vis-a-vis the fluorosulfuric acid, and thereby decreases the probability of undesirable competing side reactions which have a detrimental effect on product quality, while increasing catalyst selectively to desirable highly branched paraffinic products, thus resulting in higher quality alkylate product than would otherwise be achieved. Various moderators that can be employed in the present catalyst system are shown at column 2, lines 38-67, column 3, lines 16-68 and column 4, lines 1-23 of U.S. Pat. No. 3,887,635.

Preferred catalyst moderators contain either a hydroxy group such as alcohols or a hydroxy group precursor, such as ethers which, it is speculated, can potentially cleave to form alcohols under the acidic conditions of the subject invention. Of these, the more preferred moderators are the alcohols and water, the most preferred being water. It is noted that the catalyst moderator and the fluorosulfuric acid can be premixed prior to introduction into the reactor, thereby forming the catalyst system. The catalyst may also be formed in situ.

The exact mechanism by which the moderator compounds effectuate increased catalyst selectivity while reducing competitive side reactions is not known. However, the active catalyst species employed herein is postulated to be an equilibrium mixture comprising several components. By way of illustration, it is speculated that the addition of water to fluorosulfuric acid results in initial dissociation of the strong acid followed by hydrolysis:

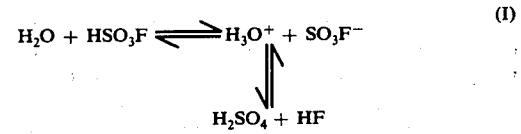

(I)

The equilibrium is believed to lie towards the right and, therefore, little, if any, free water should exist in the strong acid system. Similar mechanisms can be postulated for other moderators such as alcohols and ethers.

By the very nature of the postulated mechanism, it is clear that the manner in which the active catalytic system is formed is immaterial. Thus, in the above example, mixing HF and $H_2SO_4$ in equal molar amounts should result in the same catalyst system as would be obtained by mixing water with $HSO_3F$ in equal molar amounts. The active catalyst system may be formed by mixing HF, H₂SO₄ and HSO₃F or HF, SO₃ and H₂O in appropriate amounts. Hence, when the catalyst system is described as "being formed from" a strong acid and a moderator, it is not meant to be limited by any one catalyst formation mode; rather, this description is used merely for convenience in providing a simple definition of the active catalyst system.

The amount of moderator used in forming the catalyst system is an important variable in the production of high quality alkylate. The desired amounts of moderator will vary dependent, in part, on the alkylation temperature. Thus, for example, at temperatures between about 0° to 40° F., useful amounts of moderator can range between about 5 and 45 mole % based on acid. In some instance, however, it may be desirable to use somewhat lower or higher amount of moderator, e.g. 50 mole % based on acid, where, for example, different catalyst activity or selectivity is desired.

At high alkylation temperatures, e.g. between about 40° and 100° F., increased amount of moderator may be desirable due to the increased strong acid activity. Thus, an amount of moderator ranging between about 50 to 100 mole % based on acid may be used at these higher temperatures. In fact, under appropriate conditions, these higher amounts of moderator may also be utilized at the lower temperatures disclosed hereinabove, if desired. A preferred catalyst is one formed from fluorosulfuric acid and from about 5 to 100 mole %, based on acid, of (1) water, (2) $C_1$-$C_7$ saturated aliphatic monohydroxy alcohol or (3) a mixture of water and said alcohol.

Although the broad concentration ranges are generally independent of the type of moderator used, the preferred or optimal range will vary depending on the structure of the moderator, the reaction temperature, the concentration and nature of the olefin in the feed, the amount of organic sludge present, and the olefin space velocity and the like.

In addition to being used in classical alkylation processes as hereinabove described, the catalyst system employed herein may also be used in self-alkylation processes, which are also known as hydrogen transfer alkylation processes. The $C_4$-$C_{16}$ branched chain olefins and $C_4$-$C_8$ isoparaffins are preferred reactants. The process is generally conducted in the liquid phase whereby the isoparaffin is dimerized and the olefin is saturated to the corresponding paraffin, thus producing an alkylate-type product of high quality. Self-alkylation processes are generally described in U.S. Pat. No. 3,150,204. Undesired side reactions are minimized using these catalyst systems, thereby providing high yields of the desired products.

In general the amount of olefin contacted with the catalyst can range from about 0.05 to 1000 volumes of olefin per hour per volume of catalyst inventory in the reactor (V/V/Hr.), i.e. olefin space velocity. Preferably, the olefin space velocity ranges from about 0.05 to 10.0 V/V/Hr., and still more preferably from about 0.05 to 1.0 V/V/Hr., e.g. 0.1 V/V/Hr. The volume % of total catalyst in the reaction mixture or emulsion (when liquid phase operations are used) in the alkylation zone can range from about 30 to 80 volume % based on total reaction mixture and preferably from about 50 to 70 volume %. The isoparaffin concentration, including alkylate, in the hydrocarbon phase (in a liquid phase process) can range from about 40 to about 100 volume % based on the total volume of the hydrocarbon phase and preferably from 50 to 90 volume %. Such isoparaffin concentrations can be maintained by recycling unreacted isoparaffin to the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the yield of saturated product obtained. With this in mind, the present process, when operated in either a batch or in a continuous manner, is characterized by the use of vigorous mechanical stirring or shaking of the reactants with the catalyst.

In continuous operations, as that of the embodiment shown in the FIGURE, the reactants may be maintained at sufficient pressures and temperatures to maintain them substantially in the liquid state and then continuously forced through dispersion devices into the alkylation zone. The dispersion devices may be jets, porous thimbles and the like. The reactants are subsequently mixed with the catalyst in alkylation zone 6 by conventional mixing means (not shown) such as mechanical agitators and the like. While the alkylation reaction can be carried out at a temperature within the range of from about −80° to +100° F., fairly low reaction temperatures, preferably within the range of from about −80° to +70° F., and most preferably within the range of from about −20° to about +40° F., are usually employed. Where the reaction is carried out at temperatures about +10° F., or higher it is necessary that the reaction be conducted under superatmospheric pressure, if the reactants and/or the catalyst are to be maintained substantially in a liquid state. Typically, the alkylation reaction is conducted at pressures varying from about atmospheric to about 300 psia.

In general it is preferable to employ pressures sufficiently high to maintain the reactants in the liquid phase although a vapor phase operation is also contemplated. Autorefrigerated reactors and the like may be employed to maintain liquid phase operation.

After allowing sufficient residence time for the reaction to progress, typically on the order from about one minute to one hour or more, the reaction mixture which contains hydrocarbon and deactivated or partially deactivated catalyst (often referred to as the "emulsion mixture") is withdrawn from the alkylation zone 6 via line 10 and passed into a settling zone 12. The reaction mixture will separate in zone 12 into a heavy acid phase containing the fluorosulfuric acid, sulfuric acid, hydrogen fluoride, and moderator (assumed to be water for the purpose of illustration in the following discussion), as well as organic sludge formed during said alkylation, and a hydrocarbon phase containing the alkylate product along with smaller amounts of fluorosulfuric acid, hydrogen fluoride and water which are dispersed and/or dissolved therein. The acid phase is withdrawn from settling zone 12 via line 14 and at least a portion thereof can be recycled to alkylation zone 6 via line 8 or charged to another alkylation zone, if desired. The hydrocarbon phase is withdrawn from settling zone 12 via line 16.

The present invention will now be illustrated with reference to removing a portion of the fluorosulfuric acid from the deactivated or partially deactivated catalyst prior to contacting same with water (i.e. prestripping), as is disclosed in application S.N. 772,641, filed on the same date herewith. However, it should be clearly understood that while prestripping is a preferred embodiment of the present invention, this invention is equally applicable to regeneration processes which do not include prestripping, such as those disclosed in U.S. Pat. Nos. 3,766,293 and 3,976,759.

Referring again to the FIGURE, a purge stream of the heavy acid phase is shown being withdrawn from line 14 and being passed via line 18 into the upper portion of the prestripping zone 20 and intimately contacted with a paraffin introduced via line 22. Preferred paraffins are $C_3$–$C_6$ paraffins, more preferably $C_4$ paraffins. Normal butane is the most preferred paraffin. As a result of said contacting, a portion, preferably a major portion, of both the hydrofluoric acid and the fluorosulfuric acid are stripped from said purge stream, thereby forming a gas phase containing paraffin, fluorosulfuric acid and hydrogen fluoride and a liquid phase containing fluorosulfuric acid, organic sludge and sulfuric acid as well as traces of hydrogen fluoride. The amount of stripping agent employed is that required to remove the desired amount of fluorosulfuric acid. It should be pointed out that hydrofluoric acid and sulfuric acid are present in streams 14 and 18 because the fluorosulfuric acid is partially hydrolyzed when contacted with the moderator, e.g., water. If no moderator is employed, small amounts of water are normally introduced into the alkylation zone (e.g. with the feed) such that said partial hydrolysis will occur. Be that as it may, however, the present regeneration process is also applicable to a fluorosulfuric acid catalyst that has not been hydrolyzed.

The liquid phase then passes via line 24 to the upper portion of zone 26 wherein it is contacted with water injected via line 28 in an amount sufficient to convert the fluorosulfuric acid to free hydrogen fluoride and sulfuric acid according to the reaction:

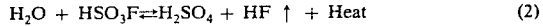

$$H_2O + HSO_3F \rightleftharpoons H_2SO_4 + HF \uparrow + Heat \qquad (2)$$

In one embodiment of the invention, it may be desirable to add up to a mole of water in excess of the stoichiometric amount required. Preferably, less than about 0.5 mole excess water is used. The resulting stream of water, hydrogen fluoride, sulfuric acid and organic sludge is then passed into the lower portion of zone 26 and intimately contacted therein with a paraffin introduced via line 30, thereby stripping hydrogen fluoride from said stream. A gas stream is shown passing from zone 26 to zone 20 via line 32.

The particular temperature and pressure employed in zones 20 and 26 are, in general, determined by economic factors such as cost or availability of stripping agent, cost of $SO_3$, etc. Normally, zone 20 should be operated at a temperature above that at which the vapor pressure of fluorosulfuric acid becomes sufficiently low such that uneconomical amounts of stripping agent are required. It is also desirable to operate both zones 20 and 26 at as high a temperature as possible because better stripping is obtained and less stripping agent is required. However, as disclosed in application Ser. No. 772,636, filed on the same date herewith, undesirable side reactions between the fluorosulfuric acid and acidic components in the catalyst (e.g. HF, $H_2SO_4$ and the like) and the hydrocarbon stripping agent become excessive at elevated temperatures, i.e. temperatures above about 250° F. Such reactions result in the formation of a polymer-like material, e.g. coke, that could "plug" the system. Thus, while elevated temperatures would normally be preferred, it has been found necessary, as disclosed in Ser. No. 772,636, to avoid contacting the acid components with the hydrocarbon stripping agent at temperatures in excess of 250° F. Therefore, as disclosed in Ser. No. 772,636, it is desirable that the temperature of zones 20 and 26 be maintained below 250° F. and in the range of from about 120° to about 250° F., preferably in the range of from about 130° to about 210° F., and more preferably in the range of from about 140° to 170° F. Total pressure of zones 20 and 26 can also vary according to the economic factors mentioned above. In general, however, the total pressure will range from about atmospheric pressure to about 170 psia, preferably to about 120 psia, and more preferably from about atmospheric to about 90 psia.

According to the present invention, a gas phase comprising paraffin, fluorosulfuric acid and hydrofluoric acid passes from zone 20 via line 34 into the lower portion of tower 36 and is cooled by contact with a vaporizable liquid paraffin from line 38, thereby forming a partially condensed vapor phase, i.e., a mixture or combination of liquid phase containing fluorosulfuric acid and vapor phase containing primarily paraffin along with hydrogen fluoride and fluorosulfuric acid. Preferably, there will be more than one, more preferably at least four, of such inlet points.

In a preferred embodiment, a series, i.e. a plurality, of such inlets 40 are located at strategic points along tower 36 to permit paraffin coolant injection of offset the heat evolved during the reaction of sulfur trioxide with hydrogen fluoride as described below so as to maintain the temperature of tower 36 relatively uniform along its length.

The liquid and vapor phases thus formed are then reacted with at least a stoichiometric amount of liquid sulfur trioxide, based on HF, from line 42 which is also introduced by at least two, preferably via a series; i.e. a plurality, of inlet 44, such as was described for the paraffin coolant, points located along the length of tower 36. While not wishing to be bound by any particular theory it is believed that the $SO_3$ dissolves in a liquid stream of fluorosulfuric acid flowing countercurrent to the flow of the vapor phase such that at least a portion, preferably a major portion, more preferably substantially all, of the hydrogen fluoride present in the vapor phase contacts said liquid stream and is converted to fluorosulfuric acid according to the reaction:

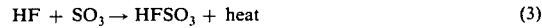

$$HF + SO_3 \rightarrow HFSO_3 + heat \qquad (3)$$

As noted above, as the gas phase from zone 20 is cooled and contacted with sulfur trioxide, it is also contacted with a countercurrently flowing liquid stream containing primarily fluorosulfuric acid, including perhaps free $SO_3$, which is introduced into the upper portion of tower 36.

Tower 36 should be operated at a temperature between that sufficient to maintain a suitable rate of reaction but below that at which excessive amounts of $SO_3$ would be volatilized into the gas phase which would result in (1) undesirable side reactions with the acid components present in the system, as disclosed in application Ser. No. 772,636 and (2) excessive carryover of sulfur trioxide in the effluent gas. In general, this corresponds to a range of temperatures from above the freezing point at which the $SO_3$ solidifies from the liquid phase to a temperature slightly above the normal boiling point of sulfur trioxide. It is important that the sulfur trioxide be introduced as a liquid. Typically, this corresponds to a temperature in the range of from about 20° to about 130° F., preferably from about 40° to about 110° F. Any convenient form of sulfur trioxide may be used, such as stabilized or unstabilized $SO_3$, or oleum. The pressure of tower 36 is not critical and will, in general, range from atmospheric to no greater than that of zone 20 or 26. Typically, a major portion of the fluorosulfuric acid contained in the gas phase 34 will be removed, i.e. recovered, in tower 36 when it is operated at the temperature and pressure conditions noted above.

A gas phase substantially depleted in fluorosulfuric acid, e.g. less than 1.0 vol %., which contains predominantly paraffin exits from the tower 36 via line 46 and it contacted with liquid paraffin injected via line 48 thereby liquefying at least a portion of the fluorosulfuric acid remaining therein. This results in a stream comprising a mixture of cooled gaseous paraffin and liquid regenerated fluorosulfuric acid. Fluorosulfuric acid may also be present in the gaseous phase, typically in amounts less than 2000 wppm. The thus cooled stream is then passed into acid recovery zone 50 which serves to form a gas phase 52 containing substantially pure paraffin, e.g., less than 1000 ppm, preferably less than 500 ppm fluorosulfuric acid, and a liquid phase 54 containing primarily regenerated fluorosulfuric acid along with some free $SO_3$ carried overhead from tower 36. The acid stream may also contain some paraffin. Preferably, however, the fluorosulfuric acid thus formed will be substantially free of paraffin, e.g., will contain less than 10,000 ppm, preferably less than 1000 wppm, more preferably less than 100 ppm of paraffin. If desired, gas phase 52 may be used as the paraffin in lines 22, 30, 38 and 48, although further processing prior to such use may be required. Liquid phase 54 is introduced into the upper portion of tower 36 and passed countercurrent to the flow of the gas phase therein. If desired, liquid sulfur trioxide may be introduced into stream 54, e.g. via line 56, to ensure that free $SO_3$ will be present in the uppermost portion of tower 36 to react with the HF therein. Aternatively, $SO_3$ could be injected into the uppermost portion of tower 36 via inlet 44.

Acid recovery zone 50 is operated at a temperature such that substantially all of the fluorosulfuric acid present in stream 46 is liquefied. This requires relatively low temperatures so as to minimize the amount of fluorosulfuric acid in the gaseous phase. The temperature in zone 50 should be sufficient to maintain two phases at the particular pressure employed. In general, this corresponds to about the dew point of the gaseous phase entering zone 50. The upper temperature is set by primarily economic consideration. Higher temperatures result in increased amounts of fluorosulfuric acid being present in gaseous phase leaving zone 50 via line 52. This, in turn, will increase the requirements of stripping agent in zones 20 and 26 in order to effect the same degree of stripping should such disposition be employed. If sufficient fluorosulfuric acid is present in line 52, the effectiveness of stripping in zones 20 and 26 would be seriously impaired and could even be rendered inoperative. When isobutane is the paraffin, the temperature in zone 50 should be maintained in the range of from about 10° to about 20° F. The pressure in zone 50 can vary broadly but, in general, should be maintained above atmospheric but below that of tower 36.

The staged paraffin cooling and $SO_3$ contacting, along with the countercurrent contacting with liquid fluorosulfuric acid, in tower 36 results in more efficient contacting between HF and $SO_3$ to regenerate fluorosulfuric acid. More particularly, the tower is a very efficient means for absorbing HF into the liquid phase and reacting same with $SO_3$. The tower also offers the advantage of minimizing the contact time between the liquid acid phase and the hydrocarbon stripping gas, thereby reducing the degradation reactions which form an organic sludge diluent in the regenerated acid. The utilization of $SO_3$ is also improved by refluxing the condensed phase from acid recovery zone 50 to tower 36 to (1) reduce the carryover of $SO_3$ therefrom and (2) return the $SO_3$ carried over to zone 50 back to tower 36 for reaction with HF. The cold condensed liquid stream from zone 50 can also provide additional cooling in tower 36, thereby giving better energy utilization. Staged $SO_3$ injection also enables lowering the $SO_3$ concentration at a particular point to a level that minimizes undesirable reactions with the hydrocarbon stripping gas as described in application Ser. No. 772,636.

Regenerated fluorosulfuric acid which may contain negligible amounts of water (typically less than 100 wppm), is withdrawn from tower 36 via line 58 and at least a portion thereof is combined with the recycle acid stream 14 for return to alkylation zone 6 via line 8. Sulfuric acid and the sludge formed during the alkylation process can be removed from the lower portion of zone 26 via line 60 and sent to sulfuric acid regeneration (not shown) for sludge removal and reconcentration, or it can be discarded. Alternately, the sulfuric acid sludge stream can be employed for removing dissolved and/or dispersed fluorosulfuric acid from hydrocarbon phase 16.

The prestripping zone, conversion/stripping zone and contacting tower are conventional equipment suitable for gas-liquid or liquid-liquid contacting. As such, they are available from various equipment vendors and do not form a part of this invention. However, Hastelloy B or C is normally employed although other stainless steels or even carbon steel may be used at lower temperatures when substantially no free water is present. The contacting tower may contain packing, trays or the like to effect staging.

The designations "prestripping zone","conversion/-stripping zone", "HF/$SO_3$ contacting tower" and "acid recovery zone" are not limited to any particular piece of equipment or configuration as a variety of equipment known to one skilled in the art can be suitably employed, provided there results substantially pure streams of gaseous paraffin and liquid regenerated fluorosulfuric acid. Thus, if desired, the paraffin prestripping and water addition steps may be effected in the same apparatus rather than separate apparatus as shown in the FIGURE.

As previously noted, hydrocarbon phase 16 contains dissolved and/or dispersed fluorosulfuric acid and hydrogen fluoride from partial dissociation of the acid, and other acidic materials such as sulfur dioxide, etc. If desired, the acid materials which are dissolved and/or dispersed in hydrocarbon phase 16 can be effectively removed by scrubbing said hydrocarbon phase with sulfuric acid. The sulfuric acid is preferably concentrated, being 98.0 to 100% $H_2SO_4$ as limited by the freezing point of the acid, but somewhat more dilute acid (95–97.9%) can also be used without substantial detriment to the efficiency of the process. The manner of scrubbing may be by any conventional means, such as by passing the sulfuric acid and hydrocarbons through a mixing orifice, a countercurrent contacting tower or by injecting them into a centrifugal pump, etc., as long as intimate contact between the hydrocarbon phase and the sulfuric acid is attained. However, countercurrent staged operations are preferred. The ratio of acid to hydrocarbon is not critical, but can vary from about 5 to 95% of the hydrocarbon stream. The temperature for scrubbing generally ranges from about 20° to 100° F. but must be greater than the freezing point of sulfuric acid. The pressure may be any pressure from atmospheric to about 500 psig. The resulting phases are settled after contacting. The hydrocarbon phase containing alkylate product may undergo further treatment to remove trace amounts of any acid materials present therein. Fluorosulfuric acid present in the sulfuric acid phase thus settled may be removed therefrom by introducing the acid phase into the upper portion of zone 20, preferably into the upper portion of zone 26.

It should be pointed out that the level of activity at which the fluorosulfuric acid catalyst should be regenerated is not only a matter of ability to catalyze the alkylation reaction, but also a matter of economics. For example, it may be desirable to regenerate a mildly deactivated catalyst to essentially fresh catalyst activity rather than allow the catalyst to be reduced to a much lower level of activity and be regenerated to fresh or to less than fresh activity. Thus, as used herein, the term "regeneration" or "regenerated" means recovering a fluorosulfuric acid catalyst that possesses a greater activity for alkylation than that possessed by the deactivated or partially deactivated catalyst. It should be understood that the regeneration process of the present invention is applicable to catalysts such as thos defined above which have lost some degree of activity and that the regeneration may only partially restore the lost activity.

Although the present regeneration process has been discussed with reference to the alkylation process and catalyst described in U.S. Pat. No. 3,887,635, it should be understood that it is applicable to any alkylation process that employs fluorosulfuric acid (see for example U.S. Pat. Nos. 3,922,319 and 3,928,487, the disclosures of which are incorporated herein by reference), including those processes that form fluorosulfuric acid from a strong acid and a moderator, e.g. mixing sulfuric acid and hydrofluoric acid in appropriate amounts (see for example U.S. Pat. No. 3,956,418).

What is claimed is:

1. In an alkylation process which comprises:
   a. contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;
   b. separating said hydrocarbon phase containing alkylate product from said fluorosulfuric acid catalyst phase the improvement which comprises regenerating said acid catalyst phase according to the following steps:
   c. stripping a portion of the fluorosulfuric acid from the acid catalyst phase separated in step (b) with a paraffin to form a stripped acid phase containing fluorosulfuric acid and said organic sludge and a gaseous phase containing paraffin and fluorosulfuric acid;
   d. contacting said stripped acid phase formed in step (c) with water to form an acid-water mixture, thereby converting at least a portion of the fluorosulfuric acid contained therein to hydrogen fluoride and sulfuric acid;
   e. stripping at least a portion of the hydrogen fluoride from said acid-water mixture formed in step (d) with a paraffin to form a gaseous phase comprising hydrogen fluoride and paraffin and a liquid phase comprising sulfuric acid and sludge;
   f. passing the gaseous phases formed in step (c) and step (e) into a contacting zone and cooling said phases therein with liquid paraffin to form a liquid-vapor mixture comprising a liquid phase containing fluorosulfuric acid and a vapor phase containing hydrogen fluoride, fluorosulfuric acid and paraffin;
   g. treating the vapor phase formed in step (f) in said contacting zone with at least a stoichiometric amount of liquid sulfur trioxide based on hydrogen fluoride, a portion of said liquid sulfur trixoide being dissolved in a liquid stream of fluorosulfuric acid flowing countercurrent to the flow of said vapor to convert the hydrogen fluoride present therein to fluorosulfuric acid, thereby forming a liquid phase of regenerated fluorosulfuric acid and a gas phase containing predominantly paraffin and a minor amount of fluorosulfuric acid;
   h. cooling the gas phase formed in step (g) to a temperature at which substantially all of the fluorosulfuric acid present therein in condensed, thereby forming a liquid phase containing predominantly regenerated fluorosulfuric acid and a gas phase containing substantially pure paraffin, and
   i. using at least a portion of the liquid phase formed in step (h) as said liquid fluorosulfuric acid stream in step (g).

2. The method according to claim 1 wherein said regenerated fluorosulfuric acid is recycled to said alkylation zone in step (a).

3. The method according to claim 1 wherein the catalyst includes a moderator in an amount of from about 5 to 100 mole %, based on acid, of (1) water, (2) a $C_1$–$C_7$ saturated aliphatic monohydroxy alcohol or (3) a mixture of water and said alcohol.

4. The method according to claim 3 wherein said moderator is water.

5. The method according to claim 1 wherein the paraffin is a $C_3$–$C_6$ paraffin.

6. The method according to claim 5 wherein the paraffin is n-butane.

7. The method according to claim 1 wherein the liquid paraffin in step (f) and the sulfur trioxide in step (g) are introduced into the contacting zone at more than one point along the length of said contacting zone.

8. The method according to claim 1 wherein the contacting of step (a) is carried out at a temperature within the range from about −80° to about +100° F. and the contacting of step (c) and step (d) is carried out at a temperature within the range from about 120° to about 250° F.

9. The method according to claim 1 wherein the acid catalyst phase of step (b) contains HF.

10. In an alkylation process which comprises:
    a. contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;

b. separating said hydrocarbon phase containing alkylate product from said fluorosulfuric acid catalyst phase, said hydrocarbon phase containing a portion of the fluorosulfuric acid;

c. washing said hydrocarbon phase with an acid comprising sulfuric acid thereby removing at least a portion of the fluorosulfuric acid from said hydrocarbon phase and separating a sulfuric acid phase containing said fluorosulfuric acid from said hydrocarbon phase containing the alkylate product, the improvement which comprises regenerating said acid catalyst phase according to the following steps:

d. stripping a portion of the fluorosulfuric acid from the acid catalyst phase separated in step (b) with a paraffin to form a stripped acid phase containing fluorosulfuric acid and organic sludge and a gaseous phase containing said paraffin and fluorosulfuric acid;

e. contacting said stripped acid phase formed in step (d) and the sulfur acid phase separated in step (c) with water to form an acid-water mixture, thereby converting at least a portion of the fluorosulfuric acid contained therein to hydrogen fluoride and sulfuric acid;

f. stripping at least a portion of the hydrogen fluoride from said acid-water mixture formed in step (e) with a paraffin to form a gaseous phase comprising hydrogen fluoride and paraffin and a liquid phase comprising sulfuric acid and organic sludge;

g. passing the gaseous phases formed in step (d) and step (f) into a contacting zone and cooling said phases therein with liquid paraffin to form a liquid-vapor mixture comprising a liquid phase containing fluorosulfuric acid and a vapor phase containing hydrogen fluoride, fluorosulfuric acid and paraffin;

h. treating the vapor phase formed in step (g) in said contacting zone with at least a stoichiometric amount of liquid sulfur trioxide based on hydrogen fluoride, a portion of said liquid sulfur trioxide being dissolved in a liquid stream of fluorosulfuric acid flowing countercurrent to the flow of said vapor to convert the hydrogen present therein to fluorosulfuric acid, thereby forming a liquid phase of regenerated fluorosulfuric acid and a gas phase containing predominantly paraffin and a minor amount of fluorosulfuric acid;

i. cooling the gas phase formed in step (h) to a temperature at which substantially all of the fluorosulfuric acid present therein is condensed, thereby forming a liquid phase containing predominantly regenerated fluorosulfuric acid and a gas phase containing substantially pure paraffin, and j. using at least a portion of the liquid phase formed in step (i) as said liquid fluorosulfuric acid stream in step (h).

11. The method according to claim 10 wherein the catalyst includes a moderator in an amount of from about 5 to 100 mole %, based on acid, of (1) water, (2) a $C_1$–$C_7$ saturated aliphatic monohydroxy alcohol or (3) a mixture of water and said alcohol.

12. The method according to claim 10 wherein the alkylation catalyst includes water as a moderator.

13. The method according to claim 10 wherein the acid of step (b) contains HF.

14. The process of claim 10 wherein the liquid paraffin of step (g) and the sulfur trioxide of step (h) are introduced into the contacting zone at more than one point along the length of said contacting zone.

15. The method according to claim 10 wherein the paraffin is $C_4$ paraffin.

16. The process of claim 10 wherein the liquid phase comprising sulfuric acid and organic sludge in step (f) is employed to wash the hydrocarbon phase in step (c).

17. In an alkylation process which comprises:

a. contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;

b. separating said hydrocarbon phase containing alkylate product from said fluorosulfuric acid catalyst phase the improvement which comprises regenerating said acid catalyst phase according to the following steps:

c. contacting at least a portion of the fluorosulfuric acid phase separated in step (b) with water to form an acid-water mixture, thereby converting at least a portion of the fluorosulfuric acid contained therein to hydrogen fluoride and sulfuric acid;

d. stripping at least a portion of the hydrogen fluoride from said acid-water mixture formed in step (c) with a paraffin to form a gaseous phase comprising hydrogen fluoride and paraffin and a liquid phase comprising sulfuric acid and sludge;

e. cooling the gaseous phase formed in step (d) in a contacting zone with liquid paraffin;

f. treating the cooled gaseous phase of step (e) in said contacting zone with at least a stoichiometric amount of liquid sulfur trioxide based on hydrogen fluoride, a portion of said liquid sulfur trioxide being dissolved in a liquid stream of fluorosulfuric acid flowing countercurrent to the flow of said gaseous phase to convert the hydrogen fluoride present therein to a fluorosulfuric acid, thereby forming a liquid phase of regenerated fluorosulfuric acid and a gas phase containing predominantly paraffin and a minor amount of fluorosulfuric acid;

g. cooling the gas phase formed in step (f) to a temperature at which substantially all of the fluorosulfuric acid present therein is condensed, thereby forming a liquid phase containing predominantly regenerated fluorosulfuric acid and a gas phase containing substantially pure paraffin, and h. using as least a portion of the liquid phase formed in step (g) as said liquid fluorosulfuric acid stream in step (f).

18. The process of claim 17 wherein the hydrocarbon phase separated in (b) is washed with an acid comprising sulfuric acid to remove at least a portion of the fluorosulfuric acid from said hydrocarbon phase, thereby forming a sulfuric acid phase containing said fluorosulfuric acid and said hydrocarbon phase containing the alkylate product, and adding said sulfuric acid phase containing said fluorosulfuric acid to said fluorosulfuric acid catalyst phase separated in step (b) to regenerate the fluorosulfuric acid present in said sulfuric acid phase.

* * * * *